(12) United States Patent
van Ninhuijs et al.

(10) Patent No.: US 9,384,880 B2
(45) Date of Patent: Jul. 5, 2016

(54) GRAVITATION COMPENSATION USING A SPHERICAL MAGNETIC SPRING

(71) Applicant: Technische Universiteit Eindhoven, Eindhoven (NL)

(72) Inventors: Bob van Ninhuijs, Panningen (NL); Bart Ludo Jozef Gysen, Enschede (NL); Jacob Willem Jansen, Waalre (NL); Elena Andreevna Lomonova, Eindhoven (NL)

(73) Assignee: Technische Universiteit Eindhoven, Eindhoven (NL)

( * ) Notice: Subject to any disclaimer, the term of this patent is extended or adjusted under 35 U.S.C. 154(b) by 1 day.

(21) Appl. No.: 14/540,388

(22) Filed: Nov. 13, 2014

(65) Prior Publication Data

US 2015/0137923 A1    May 21, 2015

Related U.S. Application Data

(60) Provisional application No. 61/904,719, filed on Nov. 15, 2013.

(51) Int. Cl.
*H01F 7/02* (2006.01)
*A61F 5/01* (2006.01)

(52) U.S. Cl.
CPC ............... *H01F 7/0231* (2013.01); *H01F 7/02* (2013.01); *H01F 7/0205* (2013.01); *H01F 7/0215* (2013.01); *A61F 5/01* (2013.01)

(58) Field of Classification Search
CPC ......... H01F 7/02; H01F 7/0205; H01F 7/021; H01F 7/0215; H01F 7/0221; H01F 7/0226; H01F 7/0231; H01F 7/0236; H01F 7/0242; H01F 7/0247; H01F 7/0252
See application file for complete search history.

(56) References Cited

U.S. PATENT DOCUMENTS

| 4,118,888 | A | * | 10/1978 | Ogawa | A63H 33/26 124/16 |
| 5,025,843 | A | * | 6/1991 | Caufield | A63B 60/62 150/160 |
| 6,477,749 | B1 | * | 11/2002 | Reiter | A41F 1/002 24/303 |
| 7,178,207 | B2 | * | 2/2007 | Wong | A41F 1/002 24/303 |
| 7,892,065 | B2 | * | 2/2011 | Vicentelli | A63H 33/108 446/108 |
| 2007/0205854 | A1 | * | 9/2007 | Kazadi | F16C 32/0429 335/306 |
| 2011/0031839 | A1 | * | 2/2011 | Fullerton | G01D 18/00 310/152 |
| 2012/0301130 | A1 | * | 11/2012 | Shi | H01F 7/06 396/428 |

FOREIGN PATENT DOCUMENTS

DE              2835441 A1 *  2/1980  .............. H01F 7/02

* cited by examiner

*Primary Examiner* — Mohamad Musleh
(74) *Attorney, Agent, or Firm* — Lumen Patent Firm

(57) ABSTRACT

A magnetic positioning device is provided that includes a first cup-shape permanent magnet having at least one permanent magnet segment conforming to the first cup-shape, where the first cup-shape permanent magnet has a first polarity, a second cup-shape permanent magnet that includes at least one permanent magnet segment conforming to the second cup-shape, where the second cup-shape permanent magnet segment has a second polarity, where the second cup-shape permanent magnet is disposed concentric to the first cup-shape permanent magnet, where the first polarity is the opposite of the second polarity or the first polarity is the same as the second polarity, where a gap separates the first cup-shape permanent magnet from the second cup-shape permanent magnet, and a connection feature, where the connection feature is disposed on the second cup-shape permanent magnet, where the connection feature is configured to connect a lever arm to the second cup-shape permanent magnet.

13 Claims, 15 Drawing Sheets

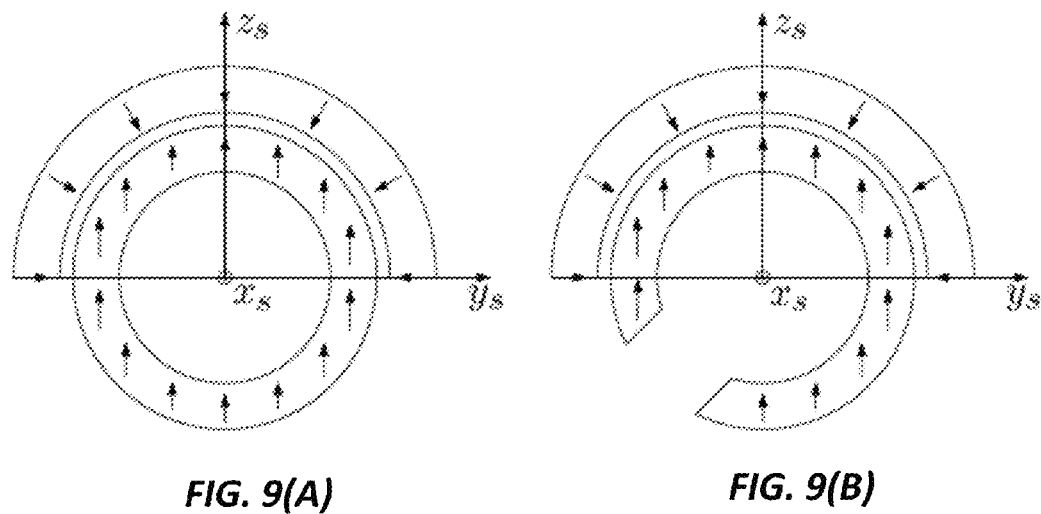
FIG. 9(A)  FIG. 9(B)
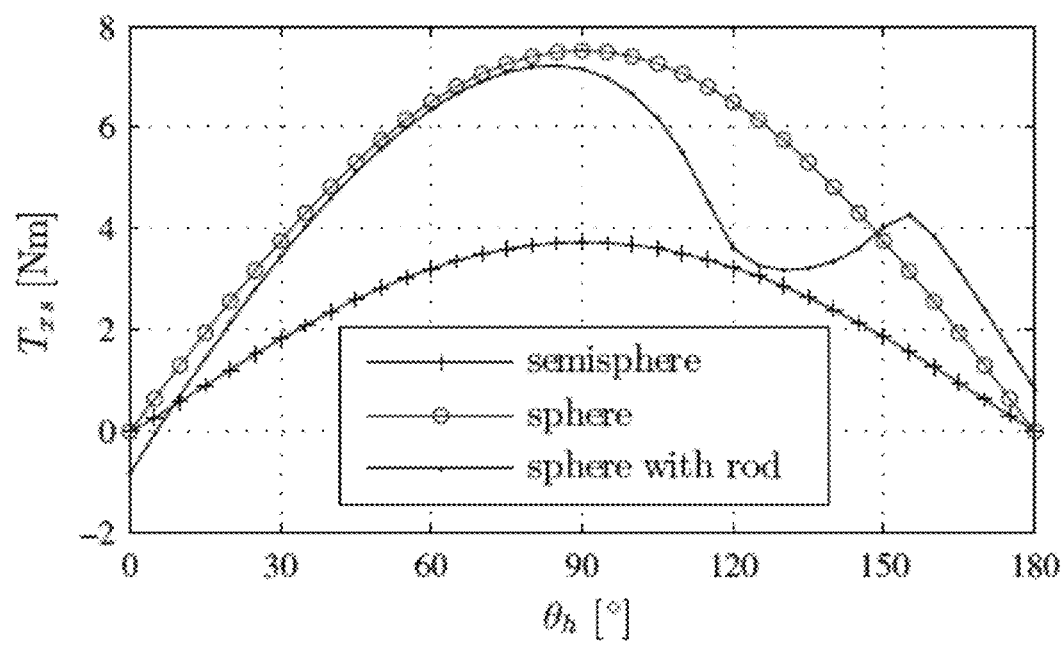
FIG. 10

Ferric material layer which may include multiple ferric material segments

Inner spherical magnet

Outer spherical magnet

Ferric material layer configurations on the spherical magnets

GRAVITATION COMPENSATION USING A SPHERICAL MAGNETIC SPRING

CROSS-REFERENCE TO RELATED APPLICATIONS

This application claims priority from U.S. Provisional Patent Application 61/904,719 filed Nov. 15, 2013, which is incorporated herein by reference.

FIELD OF THE INVENTION

The present invention relates generally to lifting devices. More particularly, the invention relates to passive gravitational force compensation in lifting devices.

BACKGROUND OF THE INVENTION

For applications that involve lifting of objects, the gravitational force is always apparent and requires either passive or active compensation. Active compensation needs external energy that flows into the system, where passive compensation uses the potential energy stored in the system.

In case of active gravity compensation, high force density actuators with high-energy consumption and potentially large moving mass are needed. Applications require often multiple degrees of freedom, which can be reached within one actuator however, usually, for every degree of freedom a separate single degree of freedom actuator is used. This results in an actuation system with an even higher volume/mass and power consumption.

In case of passive gravity compensation, mechanical springs can be used to compensate for the force of gravity. These springs can be designed to compensate for the gravity of a certain weight or a motion profile and therefore, no additional energy is required to overcome this gravitational force. The operation of a mechanical spring is affected by friction, which causes e.g. stick-slip and other non-linear phenomena. The existing mechanical springs can only provide gravity compensation at a predefined horizontal position (defined in the plane perpendicular to the gravitational force). Current applications solve this problem by adding a hinge, which lets the gravity compensation system turn to provide gravity compensation at different horizontal positions.

Mobile arm support systems provide aid during activities of daily living (ADL) such as eating, drinking and, using a computer for people with limited muscle activity. The limited muscle activity can be caused by afflictions such as neuromuscular disease or a stroke, and results in difficulties to overcome gravity or require movement assistance. Therefore, mobile arm support systems use gravity compensation to enhance the human capabilities to perform the ADL more independently. These support systems are used at home and can be mounted on a table, chair or electric wheelchair. In each of these cases no or limited electrical energy is available, therefore, passive (consumption of energy is zero) gravity compensation is beneficial. The currently available passive gravity compensators use mechanical springs, which are prestressed. These springs provide adjustable gravity compensation around a single axis. The compensation is adjusted using an electrical actuator, which varies the spring tension.

Using electrical actuators to provide support during ADL results in bulky and cumbersome arm supports, which is disadvantageous to use at home. The arm support becomes bulky because several single degree of freedom actuators are used for the shoulder joint alone. Utilizing multiple degrees of freedom actuators can decrease the heaviness and voluminous of the arm support, where spherical actuators could be used because they can mimic the shoulder joint. However, spherical actuators cannot provide the torque density needed to support the shoulder joint.

What is needed is a device that provides positioning and gravity compensation, and enables multiple axis ranges of motion without using hinges or mechanical springs.

SUMMARY OF THE INVENTION

To address the needs in the art, a magnetic positioning device is provided that includes a first cup-shape permanent magnet having at least one permanent magnet segment conforming to the first cup-shape, where the first cup-shape permanent magnet has a first polarity, a second cup-shape permanent magnet that includes at least one permanent magnet segment conforming to the second cup-shape, where the second cup-shape permanent magnet segment has a second polarity, where the second cup-shape permanent magnet is disposed concentric to the first cup-shape permanent magnet, where the first polarity is the opposite of the second polarity or the first polarity is the same as the second polarity, where a gap separates the first cup-shape permanent magnet from the second cup-shape permanent magnet, and a connection feature, where the connection feature is disposed on the second cup-shape permanent magnet, where the connection feature is configured to connect a lever arm to the second cup-shape permanent magnet.

According to one aspect of the invention, the first cup-shape permanent magnet includes at least a hemispherical shape and the second cup-shape permanent magnet has at least a hemispherical shape.

In another aspect of the invention, the first cup-shape permanent magnet has a plurality of permanent magnet segments arranged in a first cup-shape pattern, where the second cup-shape permanent magnet includes a plurality of permanent magnet segments arranged in a second cup-shape pattern. In one aspect, magnetic poles of the first polarity are oriented toward a center of the first cup-shape pattern and magnetic poles of the second polarity are oriented parallel to a polar axis of the second cup-shape pattern. In another aspect, magnetic poles of the first polarity are oriented parallel to a polar axis of the first cup-shape pattern and magnetic poles of the second polarity are oriented parallel to a polar axis of the second cup-shape pattern. In yet another aspect magnetic poles of the first polarity are oriented toward a center of the first cup-shape pattern and magnetic poles of the second polarity are oriented toward a center of the second cup-shape pattern. According to a further aspect, magnetic poles of the first polarity are oriented parallel to a polar axis of the first cup-shape pattern and magnetic poles of the second polarity are oriented toward a center of the second spherical permanent magnet.

In another aspect of the invention, the first cup-shape permanent magnet further includes a ferric material disposed on an outside surface of the first cup-shape permanent magnet. In one aspect, the ferric material includes a ferric material layer or at least one ferric material segment.

According to another aspect of the invention, the second cup-shape permanent magnet further has a ferric material disposed on an inside surface of the second cup-shape permanent magnet. According to one aspect, the ferric material includes a ferric material layer or at least one ferric material segment.

According to another aspect, the invention further includes a second connection feature that is disposed on the first cup-shape permanent magnet, where the second connection feature is configured to connect a second lever arm to the first cup-shape permanent magnet. In one aspect, the second connection feature comprises a ferric material that is magnetically disposed on the first spherical permanent magnet.

BRIEF DESCRIPTION OF THE DRAWINGS

FIGS. 9(A)-9(B) show different geometries for the radial-parallel magnetization topology, (A) sphere geometry for the inner magnet (B) sphere geometry with cutout to mount the rod for the inner magnet, according to the current invention.

FIG. 10 shows torque, $T_{xs}$, for the different inner magnet geometries: semisphere, sphere and, sphere with rod, according to the current invention.

DETAILED DESCRIPTION

Figure 1A:
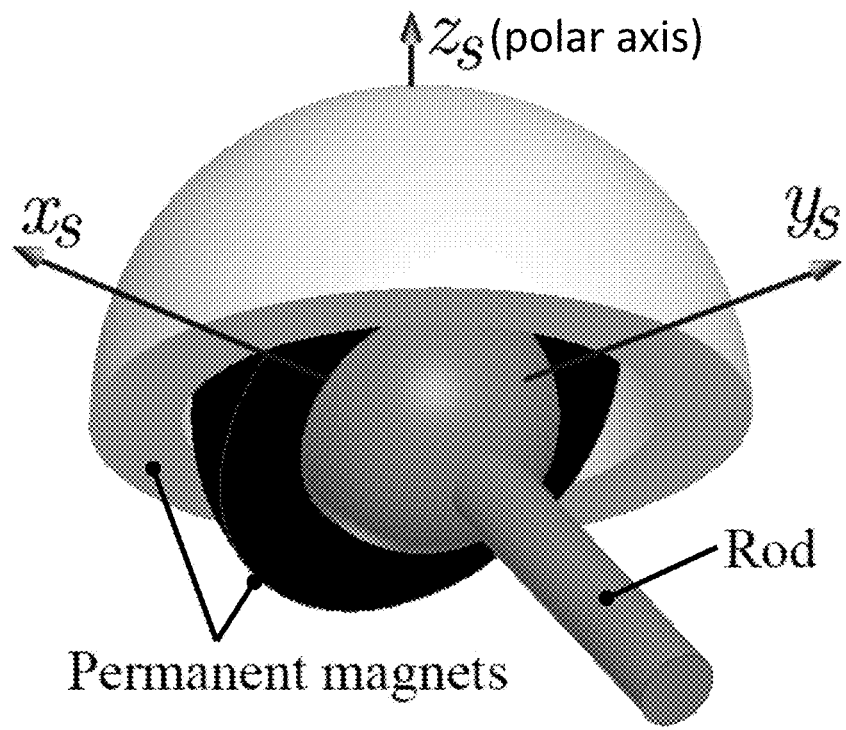
FIG. 1(A)-1(C) show schematic drawings of embodiments of a cup-shape or spherical permanent magnet positioning compensator, according to the current invention.

This current invention provides passive positioning or gravity compensation using magnetic forces, where no additional energy is required to overcome the gravity in a lifting system.

According to one embodiment, the invention provides positioning or gravity compensation at every position in the complete multi-degree-of-freedom range of motion of the device without an additional hinge or any rotation of the structure.

In case of varying loads, additional actuators can be added which only have to counteract the variation of the total gravity compensation and therefore can be significantly smaller.

In a further embodiment, the spherical magnetic spring includes spherical-like or cup-shaped structures, which are made of permanent magnets or contain permanent magnet segments. The combination of these spherical-like structures gives a construction that can be compared with a ball and socket joint. The complete structure includes one or multiple air gaps and multiple spherical-like structures, where the outside structure only partially surrounds the inside structure. The magnetization pattern(s) of the inner and outer structures are designed such that they can provide positioning or gravity compensation at every point in the complete multi-degree-of-freedom range of motion of the device.

A magnetic positioning device is provided that includes a first cup-shape permanent magnet having at least one permanent magnet segment conforming to the first cup-shape, where the first cup-shape permanent magnet has a first polarity, a second cup-shape permanent magnet that includes at least one permanent magnet segment conforming to the second cup-shape, where the second cup-shape permanent magnet segment has a second polarity, where the second cup-shape permanent magnet is disposed concentric to the first cup-shape permanent magnet, where the first polarity is the opposite of the second polarity or the first polarity is the same as the second polarity, where a gap separates the first cup-shape permanent magnet from the second cup-shape permanent magnet, and a connection feature, where the connection feature is disposed on the second cup-shape permanent magnet, where the connection feature is configured to connect a lever arm to the second cup-shape permanent magnet.

According to one aspect of the invention, the first cup-shape permanent magnet includes at least a hemispherical shape and the second cup-shape permanent magnet has at least a hemispherical shape.

In another embodiment, two spherical magnetic structures are used to form a spherical spring and where the rod is attached to the inner spherical structure, which can rotate in any direction. Due to the used magnetization of the inner and outer spherical structures, a torque around the x-axis and/or the y-axis is generated.

The combination of these spherical-like structures gives a construction that can be compared with a ball and socket joint. It can be constructed in such a way that it produces a force in the direction opposite to the gravity force in the horizontal plane at every vertical level.

Due to the configuration of the permanent magnets, the device has a stable point and a metastable point, where the system has a spring-like behavior, which means that it will return to its stable rest position when the rod is in parallel with the polar z-axis, when no external forces or masses are considered. The metastable positions can exist depending on the position of the structures and magnetization orientations used.

The interaction between the permanent magnets provides the force necessary to compensate for the gravitational force and therefore no external energy such as electricity, air pressure, etc. is necessary therefore, no power consumption is required. Furthermore, this interaction does not require any contact between the permanent magnets. Strong permanent magnets can be used to decrease the size of the structure, which results in a small sized, gravity compensation system.

The embodiments of the current invention are useful for applications that require rotation of a link/arm with multiple degrees of freedom e.g. in robotics. It can be used in e.g. robotics, lithography, automotive (help to switch between gears), consumer mechatronics, medical, industrial application etc. It can be used almost everywhere a joint with minimization of energy consumption is required.

Figure 1B:
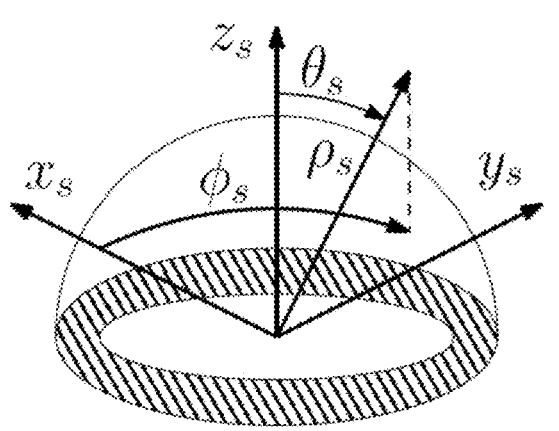
Figure 1C:
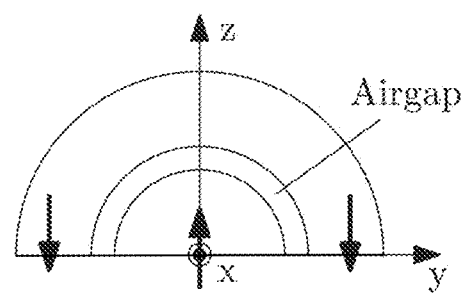

According to one embodiment, the invention provides a spherical permanent magnet gravity compensator that includes two semispherical permanent magnets as shown in FIGS. 1(A)-1(C). These spherical shapes provide compensation around two axes, which increases the flexibility compared to existing mechanical compensators.

In one exemplary embodiment, the necessary torque properties are analyzed for gravity compensation in arm support systems, where it is understood the current description of the invention applies to other positioning compensation. Different examples of magnetization topologies are provided here in, using 2D finite element analysis (FEA), to satisfy the required torque properties. With a conversion ratio the expected 3D performance is obtained with the 2D FEA results. From this 2D FEA the most suitable topology is optimized for the arm support application, according to one embodiment. The results of the optimized topology are verified using 3D FEA.

Figure 2A:
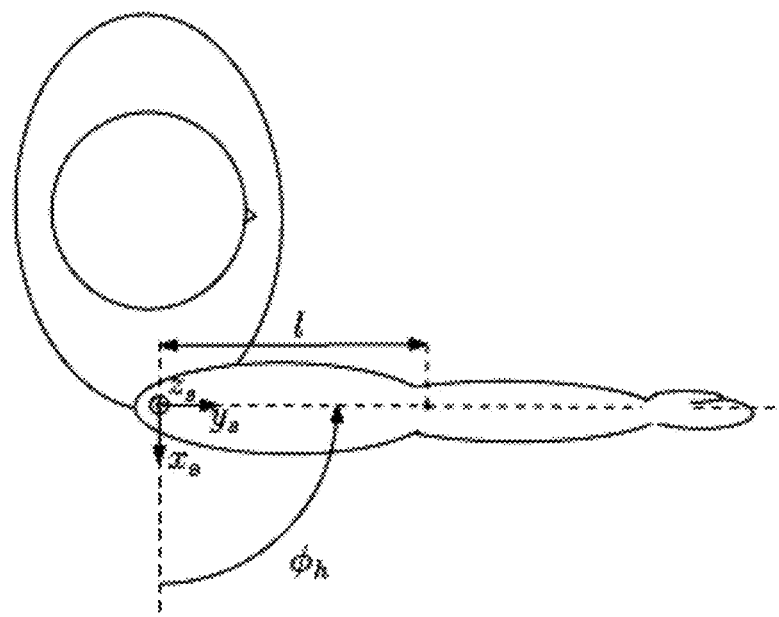
FIGS. 2(A)-2(B) show schematic representations of a human upper limb and the torque generated by the shoulder joint, (A) top view and, (B) side view.
Figure 2B:
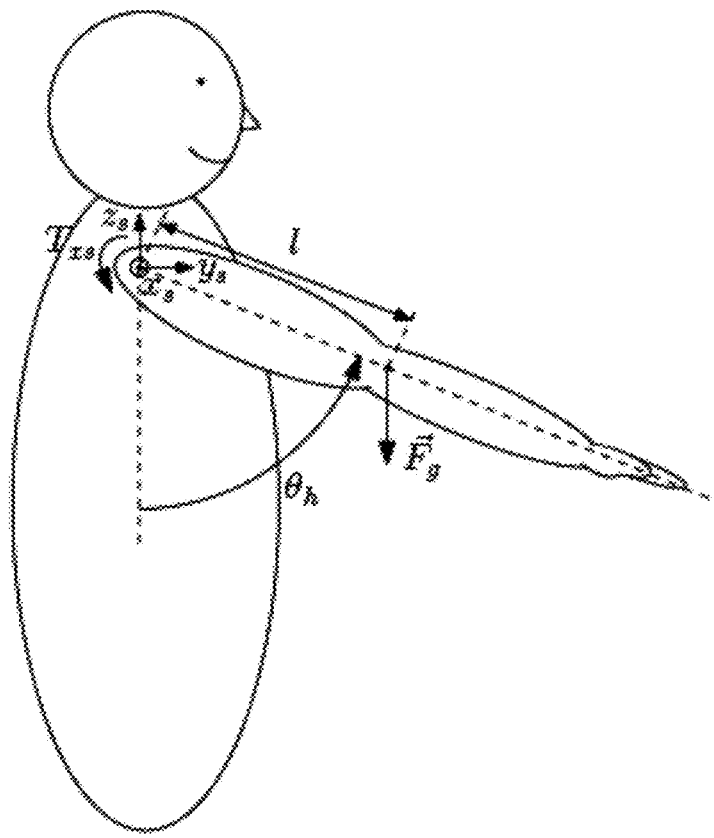

The shoulder joint can be compared to a ball and socket joint; hence, the force needed to overcome the gravity can be represented as a torque about this joint. Assuming an equal mass distribution of the human arm, the point of application of the gravity force, $\vec{F}_g$, is in the middle of the arm at a length, l, from the shoulder joint as shown in FIG. 2(B). In general, the motions for the human arm are defined for the horizontal flexion movement, $\phi_h$, as shown in FIG. 2(A) and, for the flexion/abduction movement, $\theta_h$, in FIG. 2(B). These movements can be transformed in the stationary coordinate system as defined in FIG. 1(B) by $$\theta_h = \phi_s, \quad (1)$$

$$\theta_h = 180° - \theta_s. \quad (2)$$

The torque needed to overcome the gravity, which occurs during the flexion/abduction movement, can be determined using $$T_{xs} = F_g \sin(\theta_h)\sin(\phi_h)l, \quad (3)$$

$$T_{ys} = -F_g \sin(\theta_h)\cos(\phi_h)l, \quad (4)$$

and $$T_{\phi s} = -\sin(\phi_s)T_{xs} + \cos(\phi_s)T_{ys}. \quad (5)$$

The torque, $T_{xs}$, depends on the angle $\theta_h$, where at $\theta_h=180°$ and $\theta_h=0°$ no shoulder joint torque is required to keep the human arm in position. However, at an angle of $\theta_h=90°$, a maximum shoulder joint torque is needed to overcome the gravity.

All human bodies differ from each other, therefore, to optimize and design a realistic and suitable gravity compensator, average numbers of an exemplary target group are taken into account.

The exemplary target group, which are people suffering from a neuromuscular disorder, have an average arm mass of about 3 kg and an arm length of about 0.8 m. Therefore, the application point of the gravity force, $F_g$, is situated on a distance of the shoulder at $l=0.4$ m. Hence, the gravity compensator must counterbalance for a maximum torque of $T_{max}=12$ Nm.

For this application, a range of motion of several basic ADLs is considered, such as stretching forward, drinking, eating and, using the computer. All these activities require flexion/abduction movement ranging from typically $\theta_h=0°$ to $\theta_h=90°$ and a horizontal flexion movement ranging from $\phi_h=40°$ to $\phi_h=130°$.

One embodiment of the magnetic motion or gravity compensator includes two semispherical permanent magnets, as shown in FIG. 1(A), where the inner semisphere can rotate freely in the $\theta$-direction and $\phi$-direction. From FIG. 2(B) it can be seen that at the starting position, $\theta_h=0°$, no compensation is required. By an increasing angle $\theta_h$, an increasing positive torque is needed; hence, at the starting position a metastable position is required.

An increasing torque is necessary until $\theta_h=90°$, where it reaches its maximum. From this position a decreasing torque is necessary until $\theta_h=180°$ where no torque is needed; hence, a stable position is required at $\theta_h=180°$. However, because only a limited range of motion is considered, the stable position will not be reached. Furthermore, the torque characteristic should be sinusoidal between the stable and metastable point.

Figure 15:
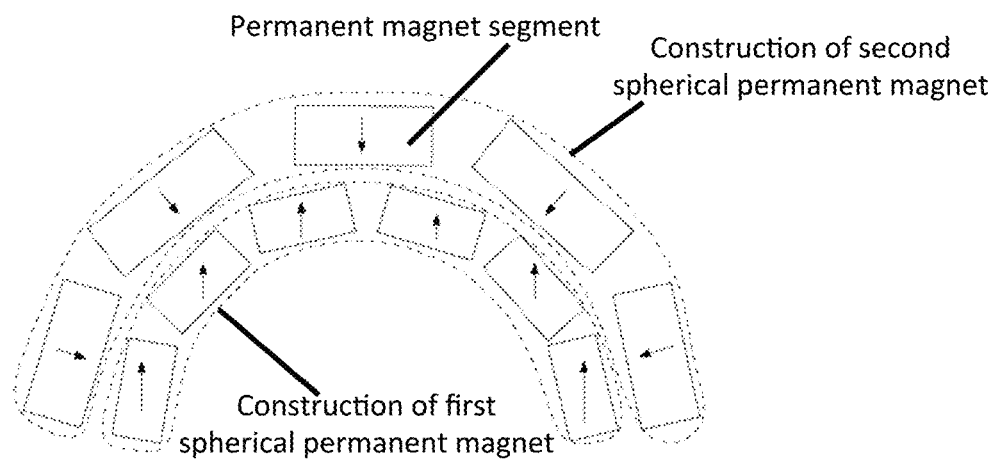
FIG. 15 shows a cross-section view of a cup-shape or spherical permanent magnet positioning compensator using permanent magnet segments, according to one embodiment of the invention.

To obtain this sinusoidal torque characteristic, different magnetizations paths are provided, as shown in FIGS. 3(A)-3(H) where, one aspect of the invention, the first cup-shape permanent magnet has at least one or a plurality of permanent magnet segments arranged in a first cup-shape pattern, where the second cup-shape permanent magnet includes at least one or a plurality of permanent magnet segments arranged in a second cup-shape pattern (see also FIG. 15). Referring now to FIGS. 3(A)-3(H), in one aspect, magnetic poles of the first polarity are oriented toward a center of the first cup-shape pattern and magnetic poles of the second polarity are oriented parallel to a polar axis of the second cup-shape pattern. In another aspect, magnetic poles of the first polarity are oriented parallel to a polar axis of the first cup-shape pattern and magnetic poles of the second polarity are oriented parallel to a polar axis of the second cup-shape pattern. In yet another aspect magnetic poles of the first polarity are oriented toward a center of the first cup-shape pattern and magnetic poles of the second polarity are oriented toward a center of the second cup-shape pattern. According to a further aspect, magnetic poles of the first polarity are oriented parallel to a polar axis of the first cup-shape pattern and magnetic poles of the second polarity are oriented toward a center of the second spherical permanent magnet. FIGS. 3(I)-3(P) show further polarity embodiments of the invention, where the polarities are arranged with the magnetic poles in opposite orientations.

Figure 4:
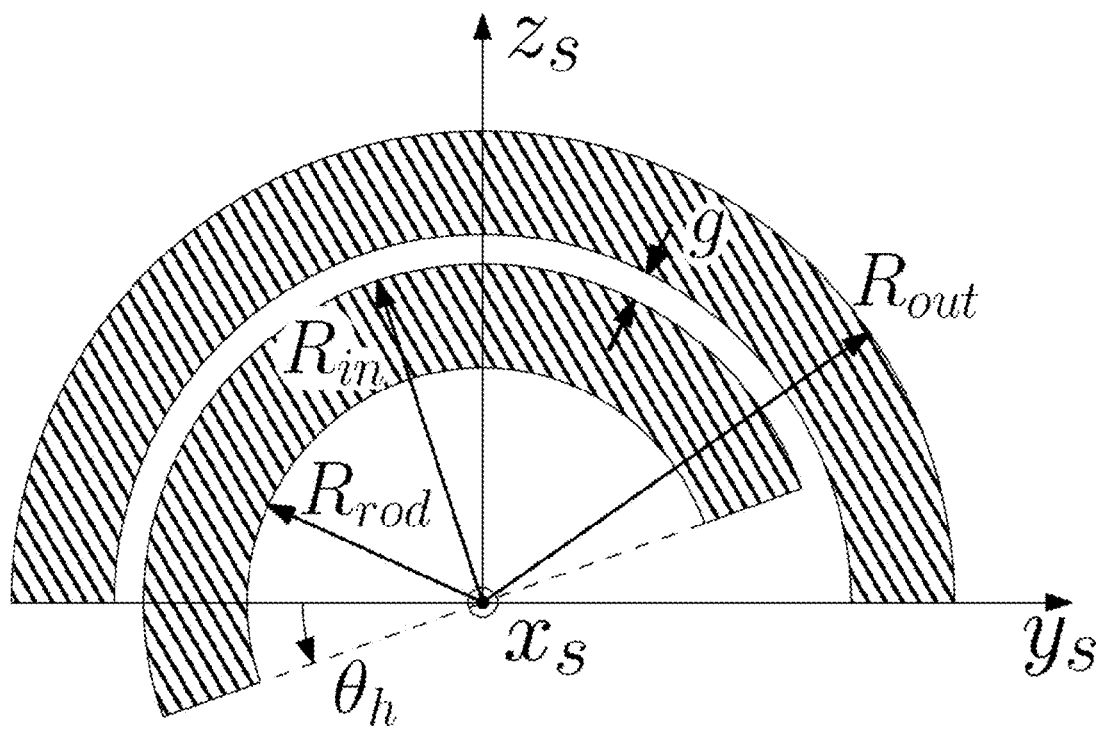
FIG. 4 shows a definition of the geometry parameters, according to one embodiment of the invention.

The initial geometry parameters for this investigation are shown in Table I and defined in FIG. 4. The torque characteristic of various combinations of parallel and radial magnetization of the two magnets is obtained. To validate the consistency of the torque characteristic, the torque of three different ratios between the inner magnet thickness and the outer magnet thickness is provided. The ratio between the two magnets is defined as $$\alpha = \frac{R_{in}}{R_{out}}. \quad (6)$$

TABLE I

INITIAL GEOMETRY PARAMETERS

| Parameter | Value | Unit | Description |
|---|---|---|---|
| $R_{rod}$ | 15 | mm | Radius of the rod |
| $R_{in}$ | 25.2 | mm | Outer radius of the inner magnet |
| g | 1 | mm | Airgap length |
| $R_{out}$ | 36 | mm | Outer radius of the outer magnet |
| $B_{rem}$ | 1.23 | T | Remanent magnetic flux density |
| $\mu_r$ | 1.05 | — | Relative permeability |

Figure 3A:
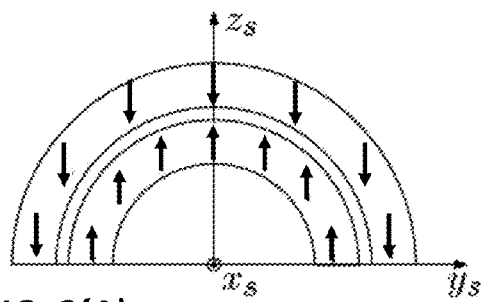
FIGS. 3(A)-3(P) show the magnetization topologies of the outer and the inner semisphere, respectively, (A, E, I, M) parallel-parallel, (B, F, J, N) radial-radial, (C, G, K, O) radial-parallel, (D, H, L, P) parallel-radial, according to embodiments of the invention.
Figure 3E:
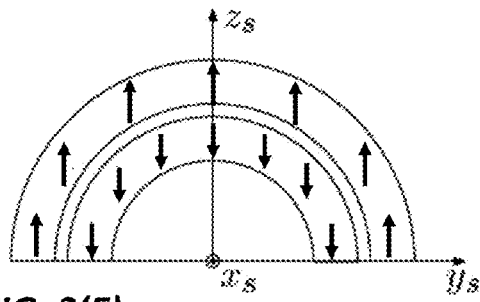
Figure 3B:
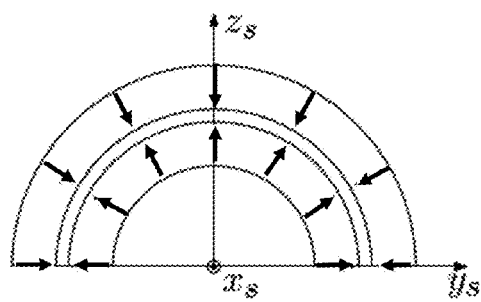
Figure 3F:
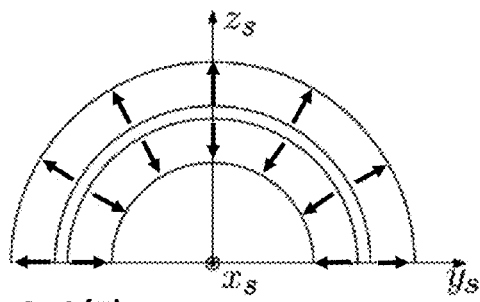
Figure 3C:
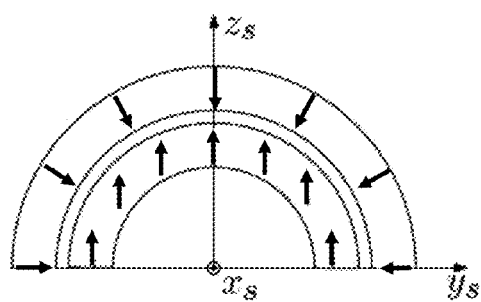
Figure 3G:
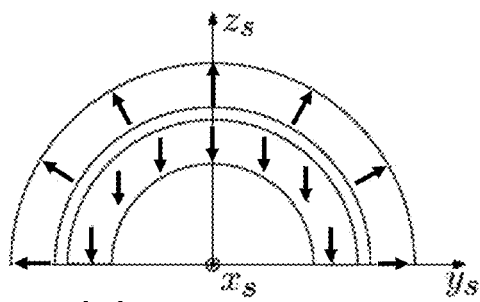
Figure 3D:
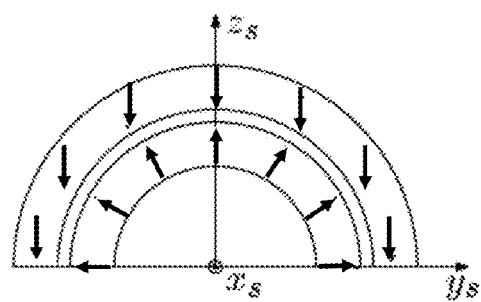
Figure 3H:
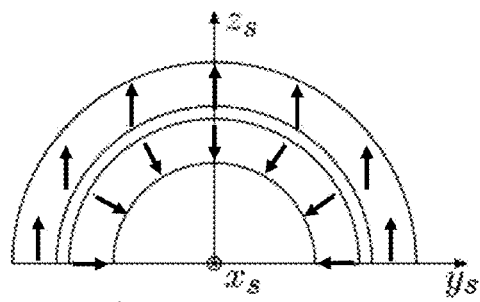
Figure 3I:
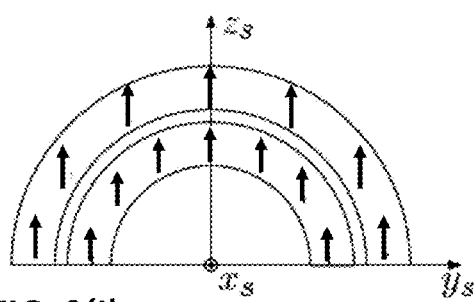
Figure 3M:
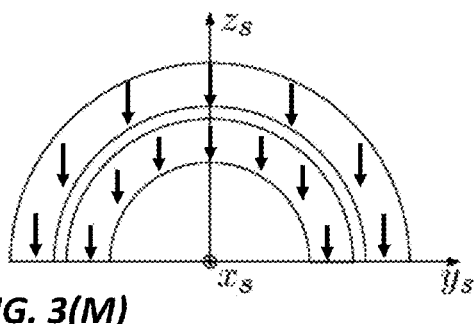
Figure 3J:
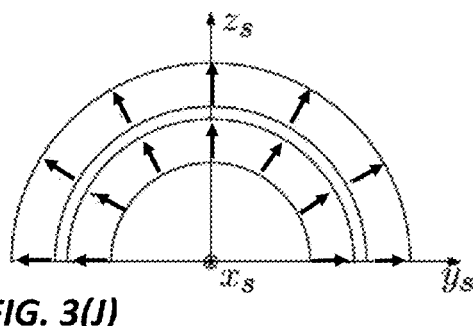
Figure 3N:
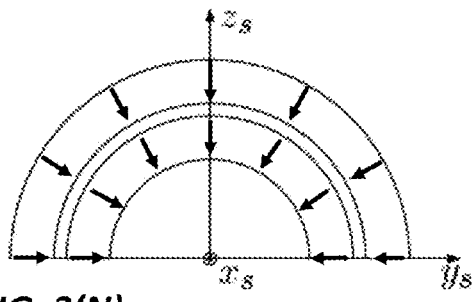
Figure 3K:
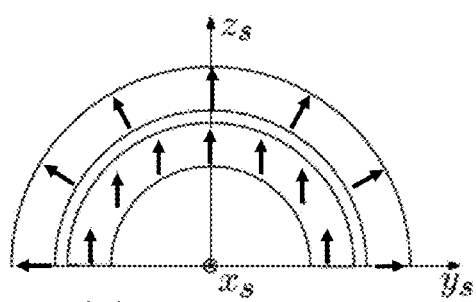
Figure 3O:
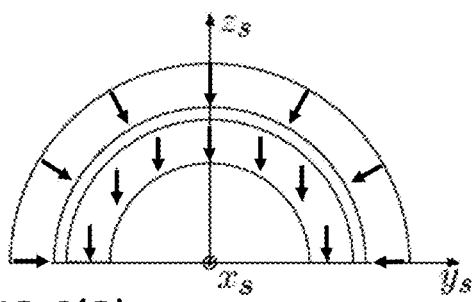
Figure 3L:
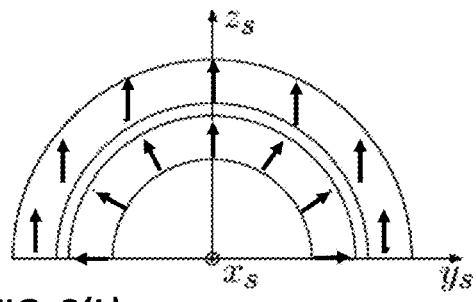
Figure 3P:
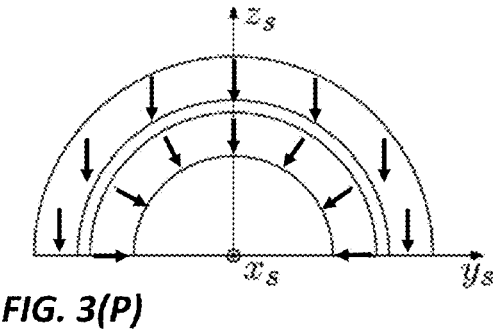
Figure 5A:
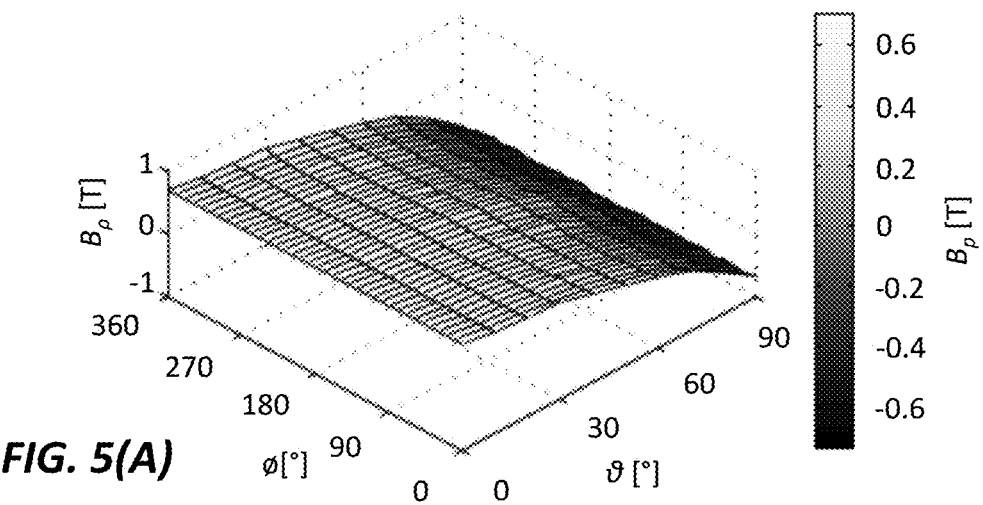
FIGS. 5(A)-5(C) show the magnetic flux density components directed to the embodiment shown in FIG. 3C in the middle of the airgap at position of $\theta_h=0°$ and $\phi_h=0°$, (A) $B_\rho$, (B) $B_\theta$, (C) $B_\phi$, according to the current invention.
Figure 5B:
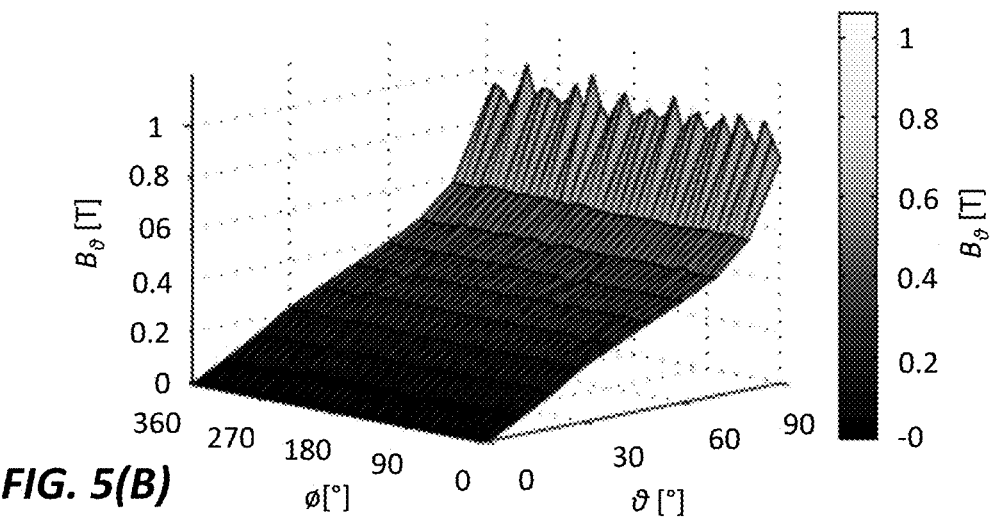
Figure 5C:
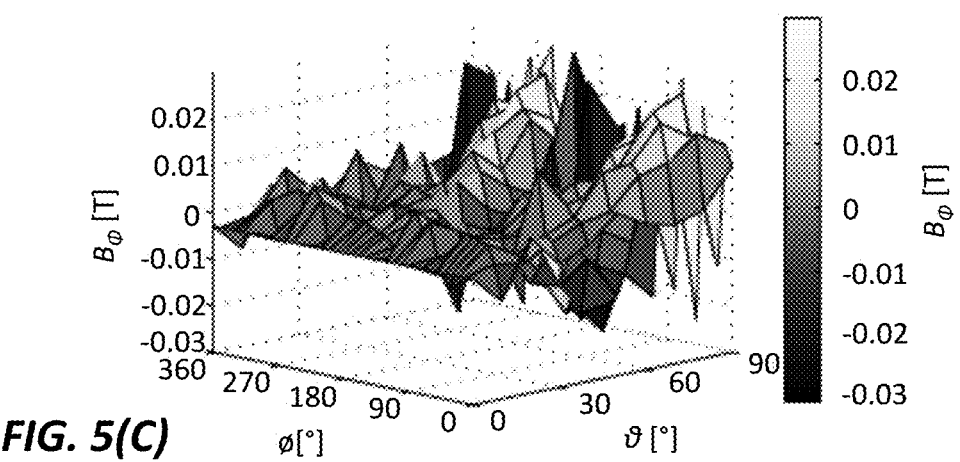

FIGS. 5A-5C show the magnetic flux density components directed to the embodiment shown in FIG. 3C in the middle of the airgap at position of $\theta_h=0°$ and $\phi_h=0°$, (A) $B_\rho$, (B) $B_\theta$, (C) $B_\phi$, according to the current invention.

Figure 6A:
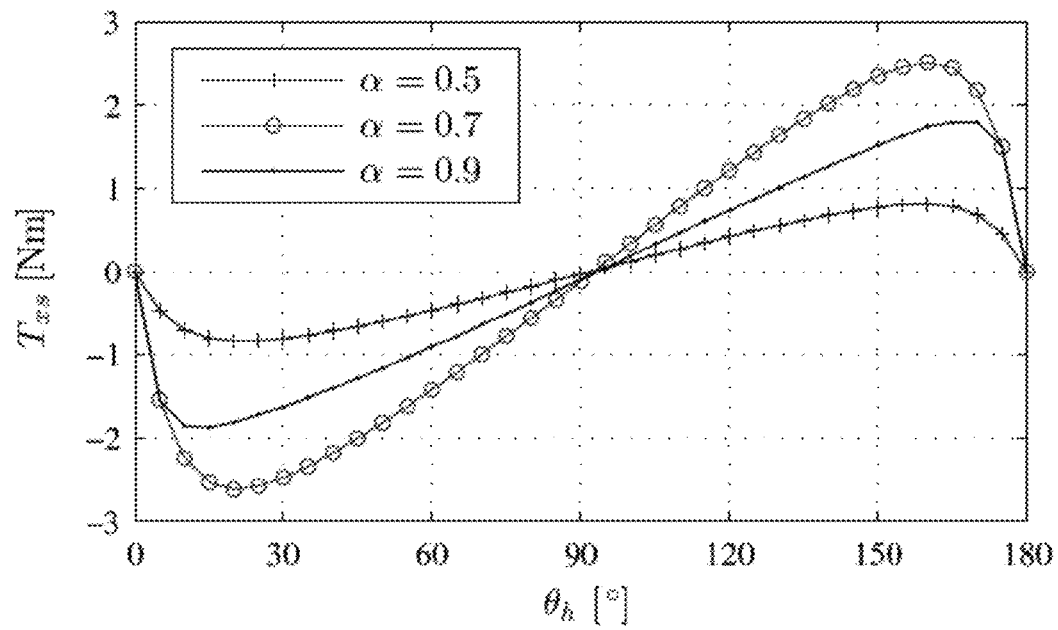
FIGS. 6(A)-6(B) show the parallel-parallel magnetization topology with, (A) the torque distribution and, (B) the flux line distribution shown for $\theta_h=20°$, according to the current invention.
Figure 6B:
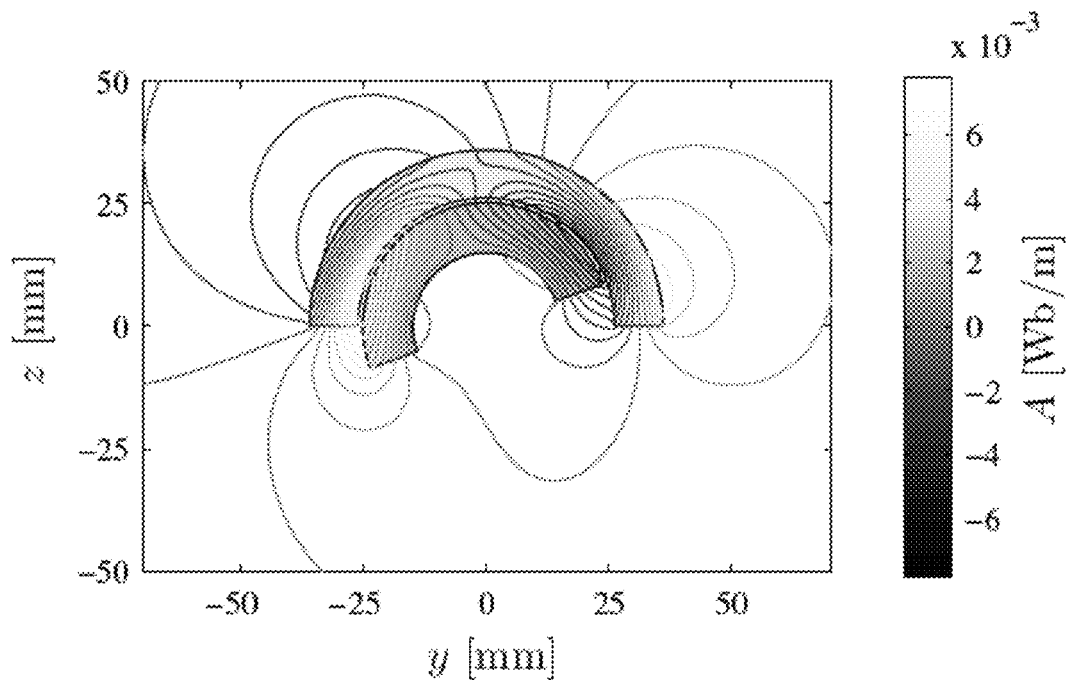

Using the parallel magnetization, for both the inner and the outer magnet, results in a torque characteristic as shown in FIG. 6(A). It can be seen that this magnetization has a linear torque characteristic within a range from $\theta_h=30°$ to $\theta_h=150°$. Furthermore, it can be seen that for the three ratios, $\alpha=0.5$, $\alpha=0.7$, and $\alpha=0.9$ only the amplitude changes and not the characteristic. The highest amount of torque is obtained with $\alpha=0.7$. Because there is no torque production at position $\theta_h=90°$ the flux lines are shown at position $\theta_h=20°$ in FIG. 6(B). Although this linear torque characteristic is not suitable for a mobile arm support, it can be valid for other applications.

Figure 7A:
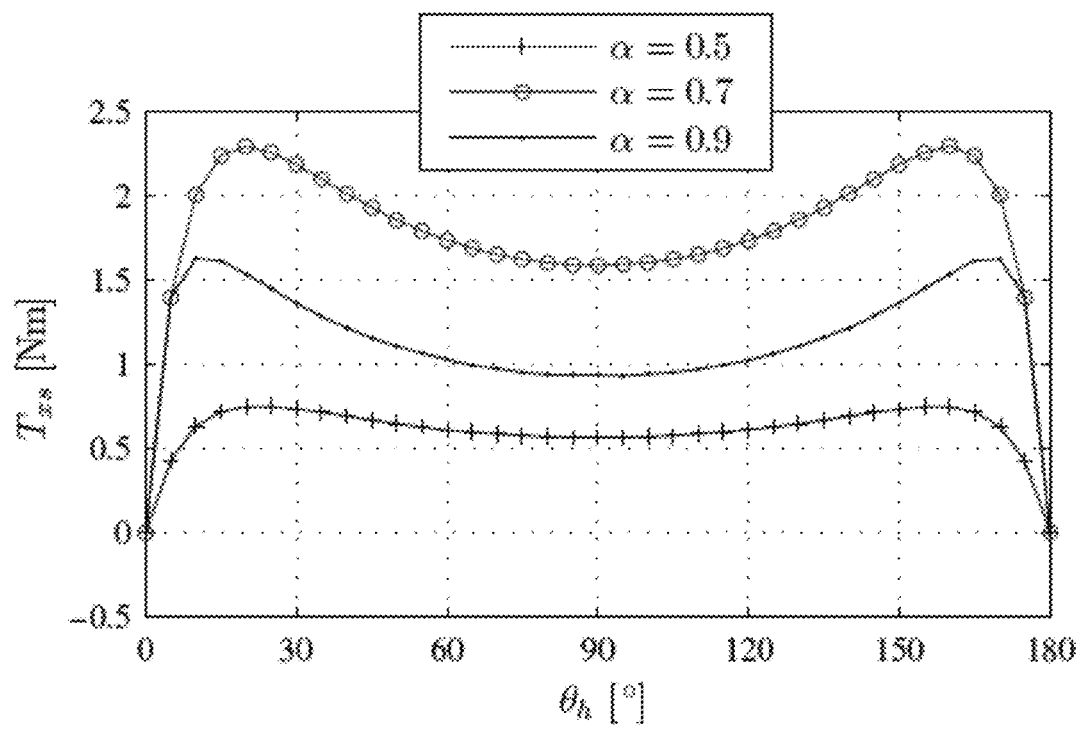
FIGS. 7(A)-7(B) show the radial-radial magnetization topology with, (A) the torque distribution and, (B) the flux line distribution shown for $\theta_h=90°$, according to the current invention.
Figure 7B:
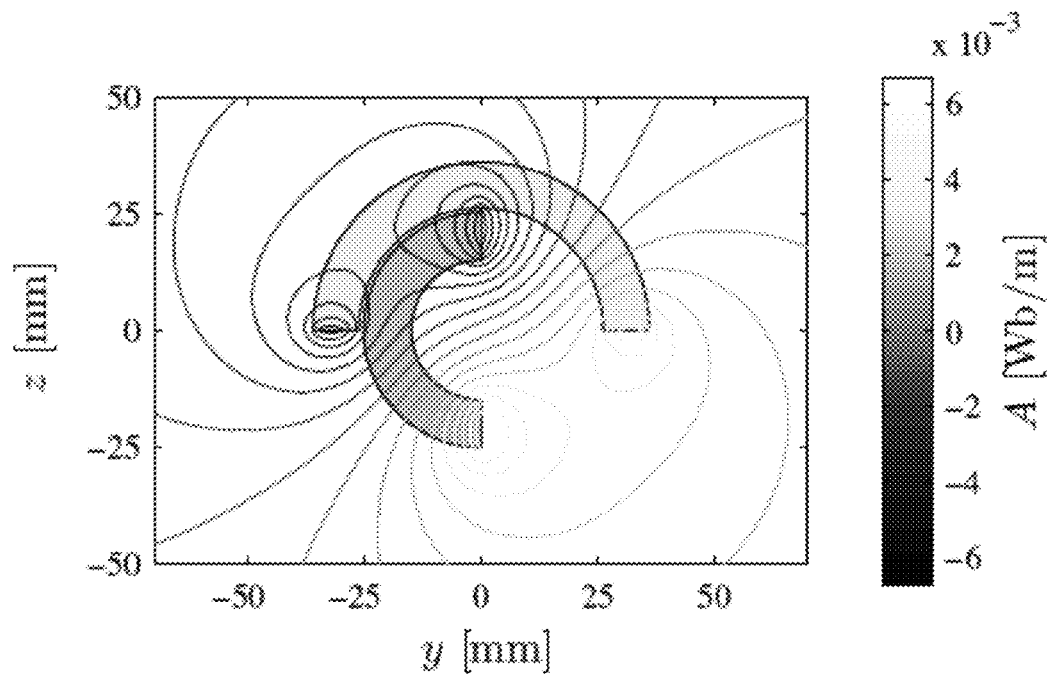

Using a radial magnetization for both magnets, results in a torque characteristic as shown in FIG. 7(A). This torque has a non-linear characteristic over the range of $\theta_h=0°$ to $\theta_h=90°$, which is also not suitable for the exemplary mobile arm support system application. Also for this magnetization topology it holds that $\alpha=0.7$ provides the highest amplitude, and there is no change in the characteristic of torque. The flux lines at a position of $\theta_h=90°$ are shown in FIG. 7(A).

Figure 8A:
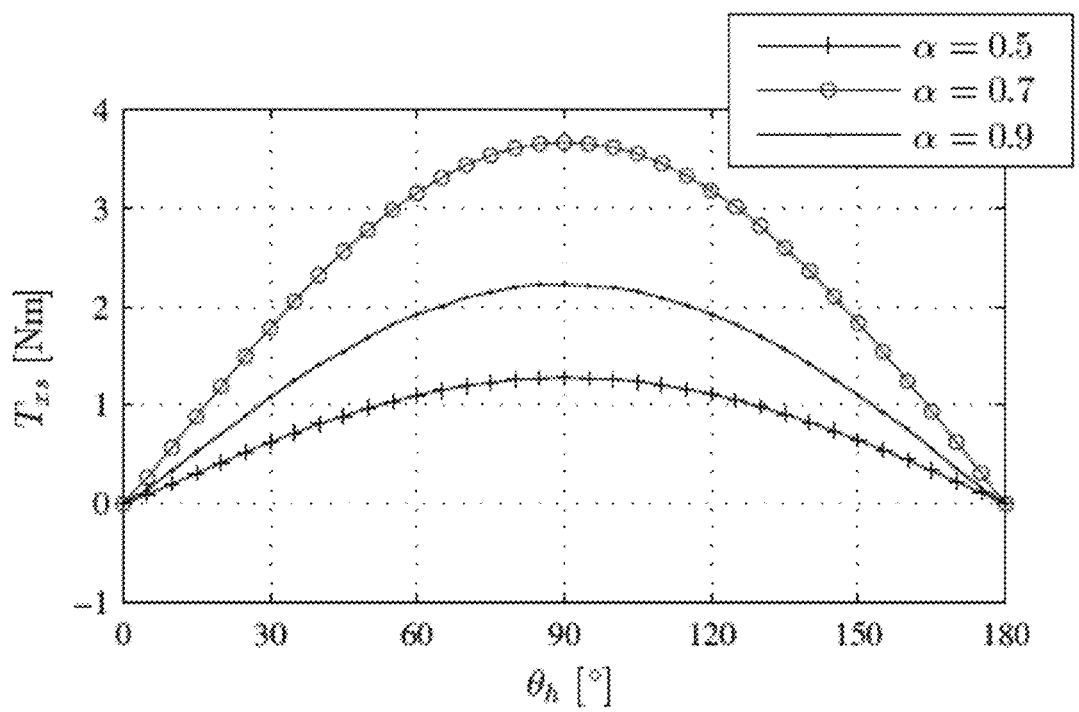
FIGS. 8(A)-8(B) show the radial-parallel magnetization topology with, (A) the torque distribution and, (B) the flux line distribution shown for $\theta_h=90°$, according to the current invention.
Figure 8B:
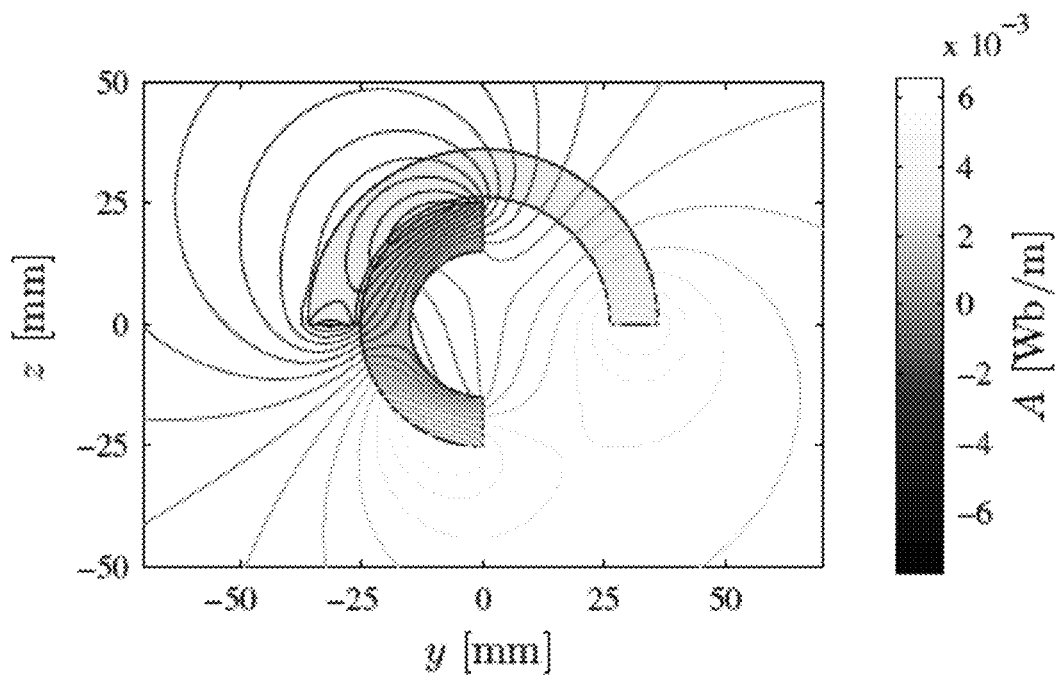

Combining these two magnetization topologies, a radial magnetization for the outer magnet and a parallel magnetization for the inner magnet, results in a torque characteristic as shown in FIG. 8(A). This figure illustrates the desired sinusoidal torque characteristic as required in (3), independently from the ratio $\alpha$. The flux lines at a position of $\theta_h=90°$ are shown in FIG. 8(A).

The topology using the radial magnetization combined with the parallel magnetization for the outer and inner magnet, respectively, is chosen because it provides the sinusoidal characteristic with the highest amplitude.

The following description considers the topology embodiment chosen as most suitable solution described above. This exemplary topology embodiment is optimized for the smallest size to reduce the costs of the magnetic gravity compensator.

To optimize the geometry for the required torque level, different inner magnet shapes are presented. A spherical magnet, as shown in FIG. 9(A), can be used as inner magnet. Because a rod is needed to exert the created torque, a full sphere is difficult to realize in practice. Therefore, a solution is shown in FIG. (B) where a segment is left out for the rod. Both torque characteristics are shown in FIG. 10 and compared with the semispherical inner magnet. It can be seen that the full sphere has almost twice the torque of a semispherical magnet and the sphere with the rod cutout no longer has sinusoidal characteristic. The error between the normalized torque and the mathematical sine function is calculated using $$\epsilon = \mathrm{rms}\left(\frac{T(\theta_h)}{\max(T)} - \sin(\theta_h)\right), \quad (20)$$

over the specified range of $\theta_h=0°$ and $\theta_h=90°$ for all three of the geometry topologies. The resulting error is shown in Table II. Ideally, the spherical shaped permanent magnet is the best topology, however, it has an unpractical geometry. The spherical shaped magnet with rod topology compensates the gravity over a range of $\theta_h=5°$ to $\theta_h=85°$.

TABLE II

THE ERROR BETWEEN THE DIFFERENT GEOMETRIES, SEMISPHERE, SPHERE AND, SPHERE WITH ROD TORQUE CHARACTERISTIC AND THE MATHEMATICAL SINE FUNCTION

| Geometry | $\epsilon$ (error) |
|---|---|
| Semisphere | 0.75% |
| Sphere | 0.006% |
| Sphere with rod | 4.3% |

Figure 11:
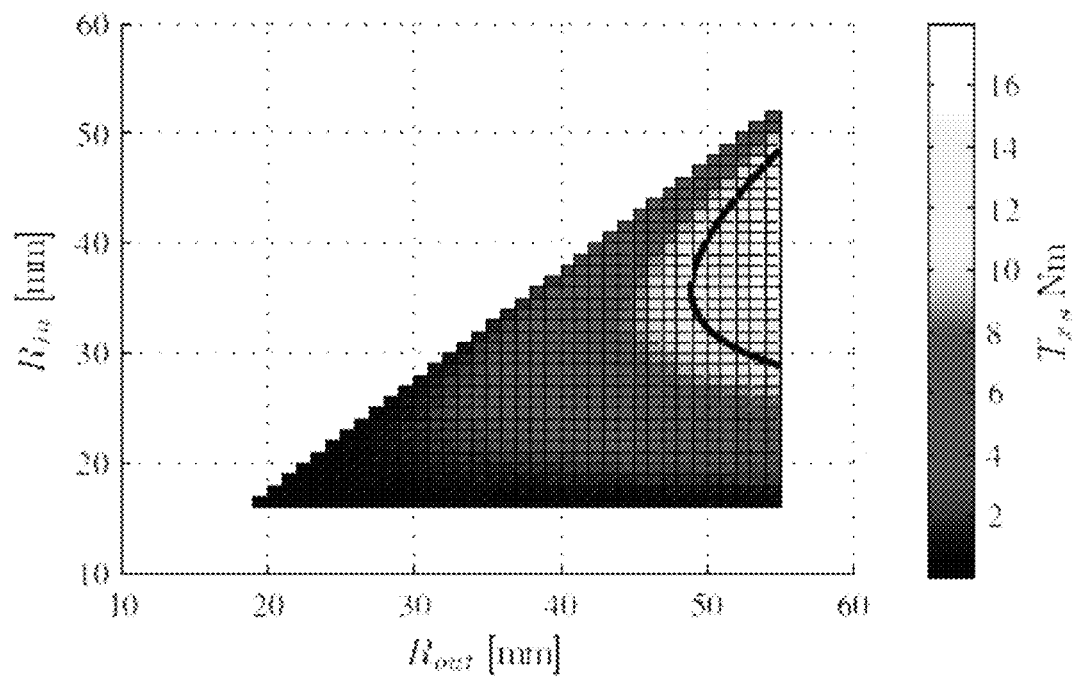
FIG. 11 shows torque, $T_{xs}$, as a function of the radii $R_{in}$ and $R_{out}$ obtained from the position of $\theta_h=90°$, where the black line represents the specifications of $T_{max}$, according to the current invention.
Figure 12:
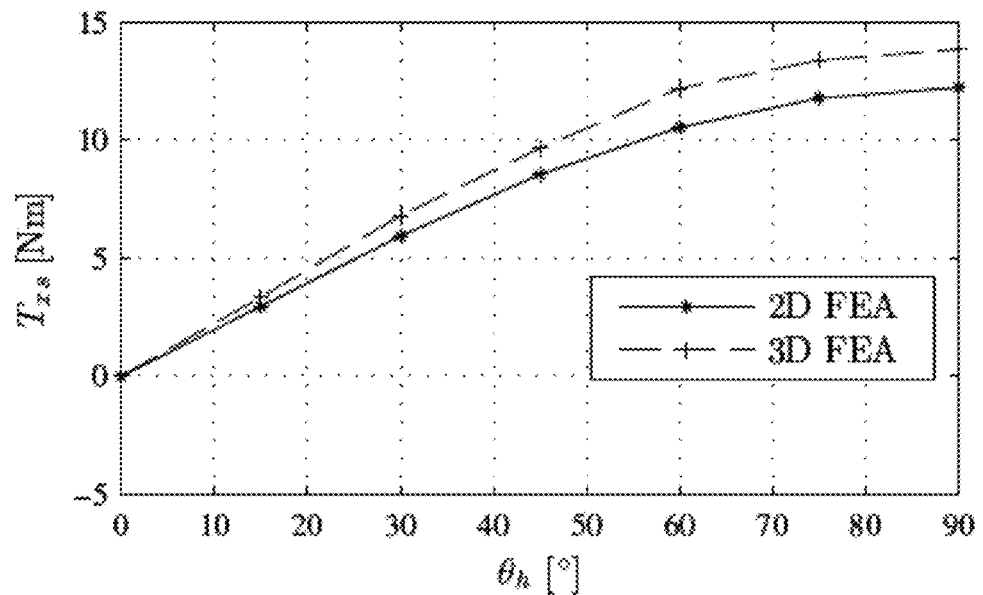
FIG. 12 shows FEA results of the 2D and 3D simulation for the optimal radii, $R_{in}=36$ mm and $R_{out}=49$ mm, according to the current invention.
Figure 13A:
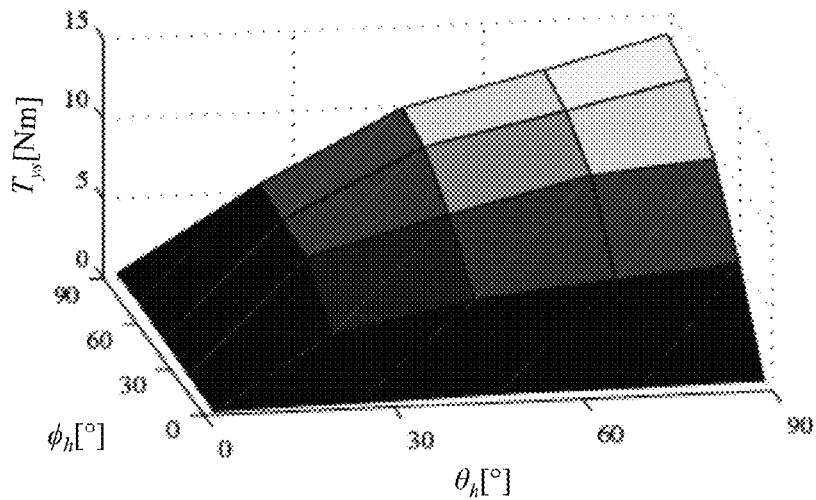
FIGS. 13(A)-13(C) show 3D FEA results for the optimal radii, $R_{in}=36$ mm and $R_{out}=49$ mm, as a function of $\theta_h$ and $\phi_h$ for (A) $T_{xs}$, (B) $T_{ys}$, (C) $T_{zs}$, according to the current invention.
Figure 13B:
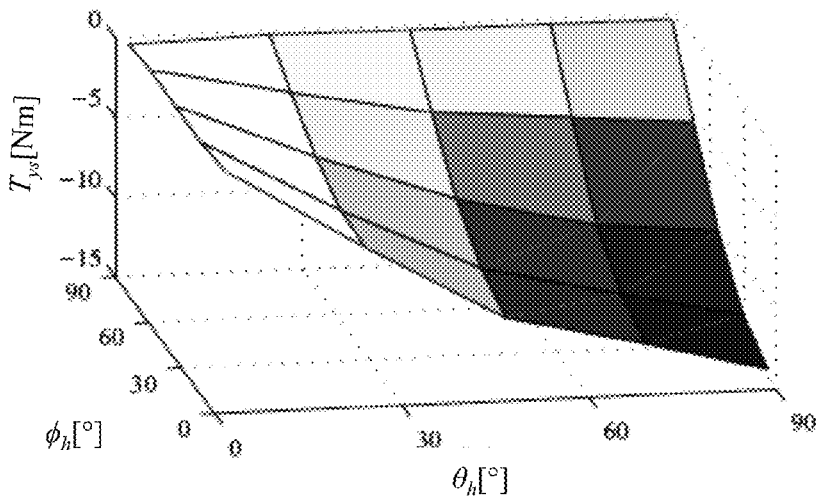
Figure 13C:
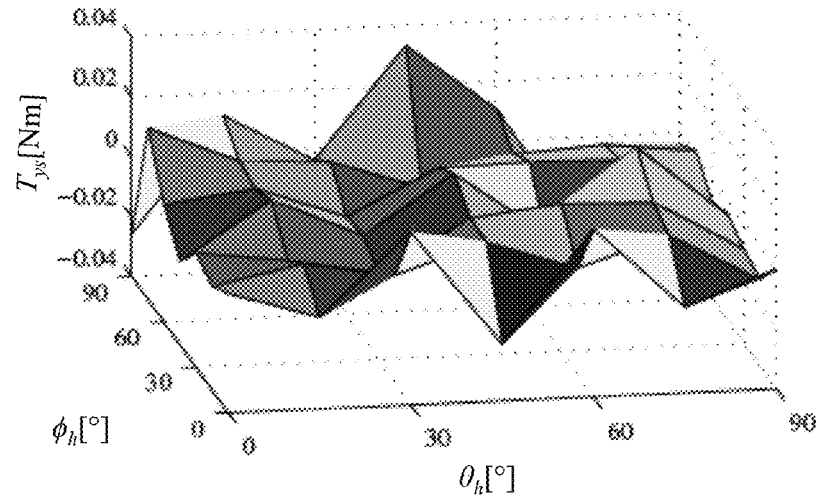
Figure 14:
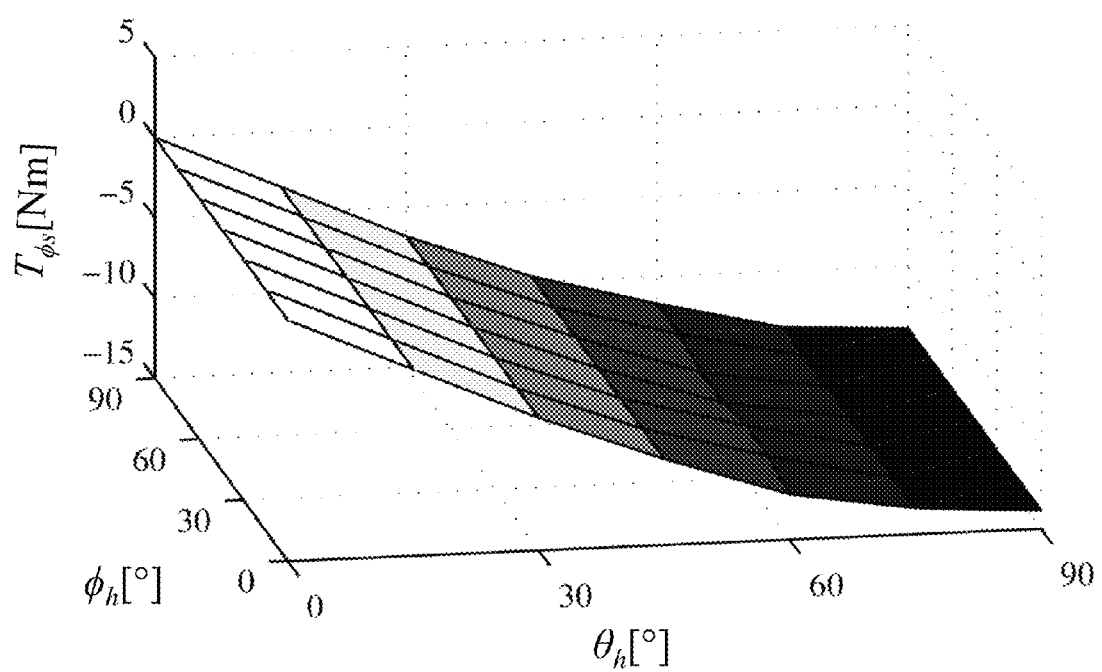
FIG. 14 shows 3D FEA results for the optimal radii, $R_{in}=36$ mm and $R_{out}=49$ mm: $T_{\phi s}$ as a function of $\theta_h$ and $\phi_h$, according to the current invention.

Some exemplary results are discussed herein, where FIG. 11 shows torque, $T_{xs}$, as a function of the radii $R_{in}$ and $R_{out}$ obtained from the position of $\theta_h=90°$, where the black line represents the specifications of $T_{max}$. FIG. 12 shows FEA results of the 2D and 3D simulation for the optimal radii, $R_{in}=36$ mm and $R_{out}=49$ mm. FIGS. 13A-13C show 3D FEA results for the optimal radii, $R_{in}=36$ mm and $R_{out}=49$ mm, as a function of $\theta_h$ and $\phi_h$ for (A) $T_{xs}$, (B) $T_{ys}$, (C) $T_{zs}$. FIG. 14 shows 3D FEA results for the optimal radii, $R_{in}=36$ mm and $R_{out}=49$ mm: $T_{\phi s}$ as a function of $\theta_h$ and $\phi_h$.

From torque results of $T_{xs}$, and, $T_{ys}$ as shown in FIGS. 13(A) and, 13(B), it can be seen that the characteristic is in agreement with (3) and (4), respectively. The torque $T_{zs}$ is shown in FIG. 13(C) and is numerical noise. The spherical torque $T_{\phi s}$ is shown in FIG. 14, it can be seen that this torque is independent of $\theta_h$ and has the expected sinusoidal characteristic.

FIG. 15 shows a cross-section view of a cup-shape or spherical permanent magnet positioning compensator using permanent magnet segments, according to one embodiment of the invention.

Figure 16:
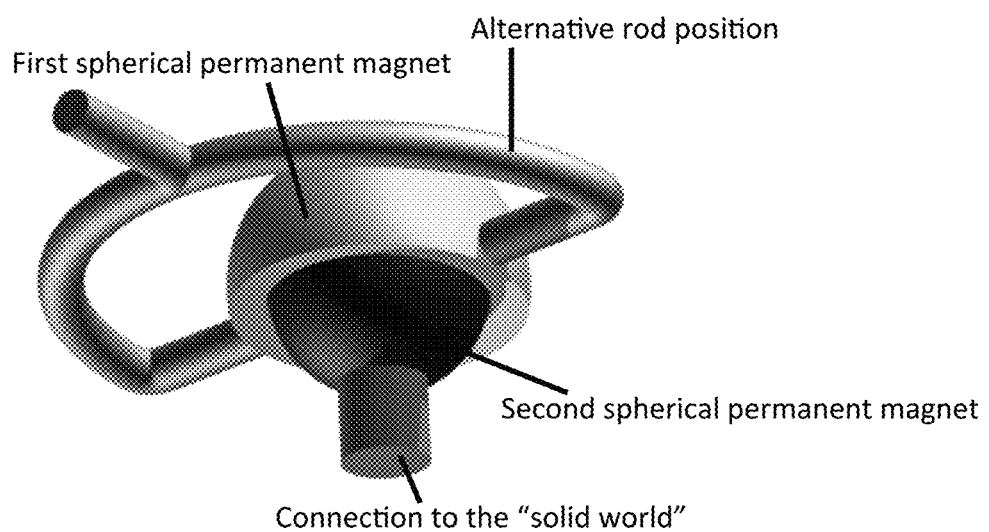
FIG. 16 shows a cup-shape or spherical permanent magnet positioning compensator having attachment features on both the inner and outer cup-shape or spherical permanent magnets, according to one embodiment of the invention.

According to another aspect, the invention further includes a second connection feature that is disposed on the first cup-shape permanent magnet, where the second connection feature is configured to connect a second lever arm to the first cup-shape permanent magnet. In one aspect, the second connection feature comprises a ferric material that is magnetically disposed on the first spherical permanent magnet, or the second connection feature comprises material other than ferric material. FIG. 16 shows a cup-shape or spherical permanent magnet positioning compensator having attachment features on both the inner and outer cup-shape or spherical permanent magnets, according to one embodiment of the invention.

In another aspect of the invention, the first cup-shape permanent magnet further includes a ferric material disposed on an outside surface, an inside surface, or the outside surface and the inside surface of the first cup-shape permanent magnet. In one aspect, the ferric material includes a ferric material layer or at least one ferric material segment.

Figure 17A:
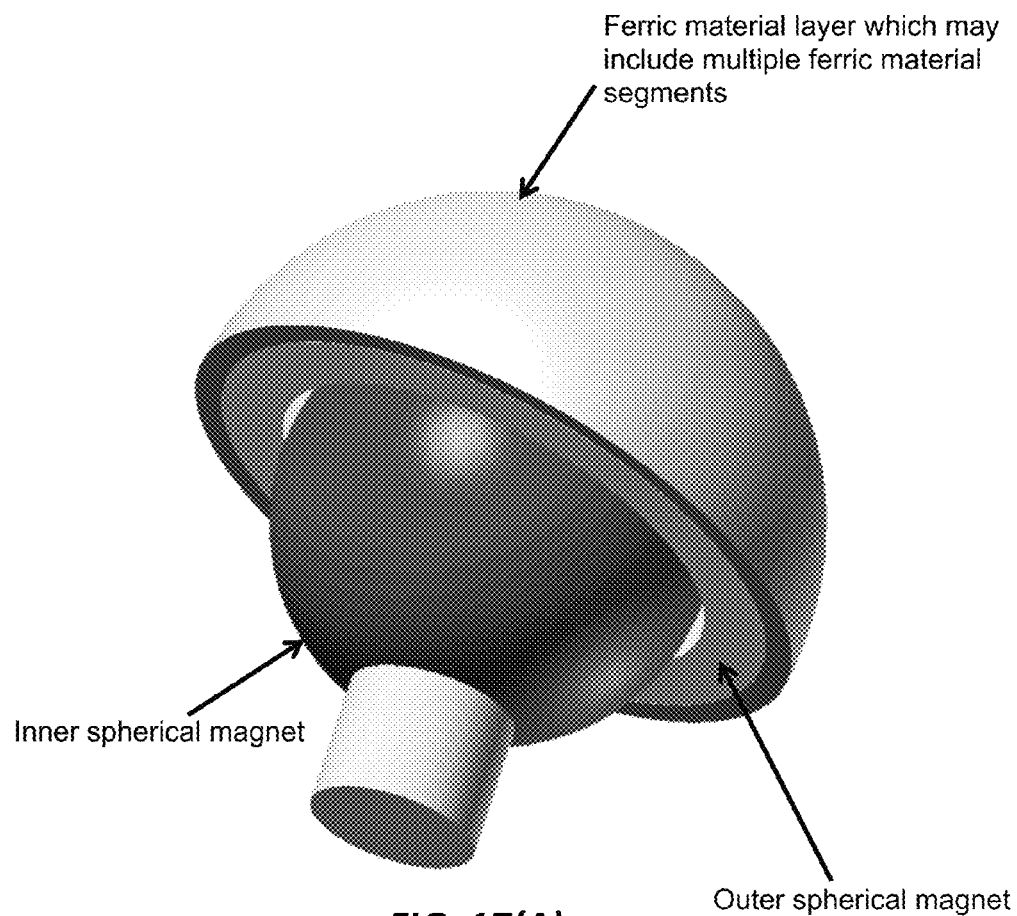
FIG. 17(A)-17(B) show the second connection feature being a ferric material that is magnetically disposed on the surfaces of the spherical permanent magnet(s), according to embodiments of the invention.
Figure 17B:
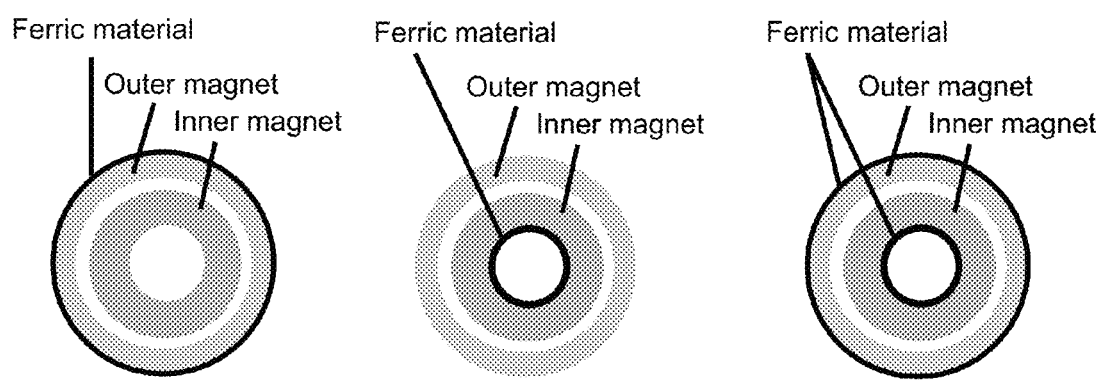

According to another aspect of the invention, the second cup-shape permanent magnet further has a ferric material disposed on an outside surface, an inside surface, or the outside surface and the inside surface of the second cup-shape permanent magnet. According to one aspect, the ferric material includes a ferric material layer or at least one ferric material segment. FIG. 17(A)-17(B) show the second connection feature or a shielding being a ferric material that is magnetically disposed on the surfaces of the spherical permanent magnet(s), according to embodiments of the invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example by change the polarity of only one of cup-shape magnets as shown in FIGS. 3(A)-3(H), the stable and metastable point will change, which creates a device which can generate gravity, where FIGS. 3(I)-3(P) show further polarity embodiments of the invention.

All such variations are considered to be within the scope and spirit of the present invention as defined by the following claims and their legal equivalents.

What is claimed:

1. A magnetic positioning device, comprising:
    a. a first sphere-shape permanent magnet comprising at least one permanent magnet segment conforming to said first sphere-shape, wherein said first sphere-shape permanent magnet comprises a first polarity; and
    b. a second sphere-shape permanent magnet comprising at least one permanent magnet segment conforming to said second sphere-shape, wherein said second sphere-shape permanent magnet segment comprises a second polarity, wherein said second sphere-shape permanent magnet is disposed inside and concentric to said first sphere-shape permanent magnet, wherein said first polarity is the opposite of said second polarity or said first polarity is the same as said second polarity, wherein a gap separates said first sphere-shape permanent magnet from said second sphere-shape permanent magnet, wherein said second sphere-shape permanent magnet is displaceable in a range from 0 to 360-degree angle $\Phi_s$ with respect to a polar axis $Z_s$ of said first sphere-shape permanent magnet and is displaceable in a range from +90-degree to a −90-degree angle $\theta_h$ with respect to said polar axis $Z_s$, wherein a restoring force is formed by said displacement of second sphere-shape permanent magnet disposed concentrically inside said first sphere-shape permanent magnet, wherein said restoring force comprises a torque about the magnetic positioning device.

2. The magnetic positioning device of claim 1, wherein said first sphere-shape permanent magnet comprises at least a hemispherical shape and said second sphere-shape permanent magnet comprises at least a hemispherical shape.

3. The magnetic positioning device of claim 1, wherein said first sphere-shape permanent magnet comprises a plurality of permanent magnet segments arranged in a first sphere-shape pattern, wherein said second sphere-shape permanent magnet comprises a plurality of permanent magnet segments arranged in a second sphere-shape pattern.

4. The magnetic positioning device of claim 3, wherein magnetic poles of said first polarity are oriented toward a center of said first sphere-shape pattern and magnetic poles of said second polarity are oriented parallel to a polar axis of said second sphere-shape pattern.

5. The magnetic positioning device of claim 3, wherein magnetic poles of said first polarity are oriented parallel to a polar axis of said first sphere-shape pattern and magnetic poles of said second polarity are oriented parallel to a polar axis of said second sphere-shape pattern.

6. The magnetic positioning device of claim 3, wherein magnetic poles of said first polarity are oriented toward a center of said first sphere-shape pattern and magnetic poles of said second polarity are oriented toward a center of said second sphere-shape pattern.

7. The magnetic positioning device of claim 3, wherein magnetic poles of said first polarity are oriented parallel to a polar axis of said first sphere-shape pattern and magnetic poles of said second polarity are oriented toward a center of said second spherical permanent magnet.

8. The magnetic positioning device of claim 1, wherein said first sphere-shape permanent magnet further comprises a ferric material disposed on an outside surface, an inside surface, or said outside surface and said inside surface of said first sphere-shape permanent magnet.

9. The magnetic positioning device of claim 8, wherein said ferric material comprises a ferric material layer or at least one ferric material segment.

10. The magnetic positioning device of claim 1, wherein said second sphere-shape permanent magnet further comprises a ferric material disposed on an outside surface, an inside surface, or said outside surface and said inside surface of said second sphere-shape permanent magnet.

11. The magnetic positioning device of claim 10, wherein said ferric material comprises a ferric material layer or at least one ferric material segment.

12. The magnetic positioning device of claim 1 further comprises a connection feature, wherein said connection feature is disposed on said first sphere-shape permanent magnet, said second sphere-shape permanent magnet, or said first sphere-shape permanent magnet and said second sphere-shape permanent magnet.

13. The magnetic positioning device of claim 12, wherein said connection feature comprises a ferric material that is magnetically disposed on said first sphere-shape permanent magnet, said second sphere-shape permanent magnet, or said first sphere-shape permanent magnet and said second sphere-shape permanent magnet.

* * * * *